(12) United States Patent
Mauro et al.

(10) Patent No.: US 10,092,220 B2
(45) Date of Patent: Oct. 9, 2018

(54) SYSTEM AND METHOD FOR MOTION CAPTURE

(71) Applicant: Telecom Italia S.p.A., Milan (IT)

(72) Inventors: Alessandro Mauro, Oggebbio (IT); Corrado Azzaro, Oggebbio (IT); Giovanni Albani, Oggebbio (IT); Claudia Ferraris, Turin (IT); Roberto Nerino, Turin (IT); Antonio Chimienti, Turin (IT); Giuseppe Pettiti, Turin (IT); Laura Contin, Turin (IT)

(73) Assignee: Telecom Italia S.p.A., Milan (IT)

( * ) Notice: Subject to any disclaimer, the term of this patent is extended or adjusted under 35 U.S.C. 154(b) by 194 days.

(21) Appl. No.: 15/126,904

(22) PCT Filed: Mar. 20, 2014

(86) PCT No.: PCT/EP2014/055591
§ 371 (c)(1),
(2) Date: Sep. 16, 2016

(87) PCT Pub. No.: WO2015/139750
PCT Pub. Date: Sep. 24, 2015

(65) Prior Publication Data
US 2017/0086712 A1    Mar. 30, 2017

(51) Int. Cl.
*H04N 7/18*    (2006.01)
*A61B 5/11*    (2006.01)
(Continued)

(52) U.S. Cl.
CPC .......... *A61B 5/1127* (2013.01); *A61B 5/0077* (2013.01); *A61B 5/1101* (2013.01);
(Continued)

(58) Field of Classification Search
CPC ............ G06K 9/00536; G06K 9/00355; A61B 5/1113; A61B 5/1127; A61B 5/744; A63F 13/428
(Continued)

(56) References Cited

U.S. PATENT DOCUMENTS

| 6,128,003 A | * | 10/2000 | Smith | ................. G06K 9/00355 345/156 |
|---|---|---|---|---|
| 7,372,977 B2 | | 5/2008 | Fujimura et al. | |

(Continued)

FOREIGN PATENT DOCUMENTS

| WO | 2013/109608 A2 | 7/2013 |
|---|---|---|
| WO | 2013/109609 A2 | 7/2013 |

OTHER PUBLICATIONS

Feb. 12, 2015—(WO) Written Opinion of the ISA and ISR—App PCT/EP2014/055591.
(Continued)

*Primary Examiner* — Gims S Philippe
(74) *Attorney, Agent, or Firm* — Banner & Witcoff, Ltd.

(57) ABSTRACT

A motion capture system includes a wearable device (e.g. a glove) suitable for being worn by a user and including one or more markers having respective colors. A video camera acquires a sequence of color frames of the user moving while wearing the glove, while a range camera acquires corresponding depth frames of the same scene. A processing unit processes both color frames and depth frames for reconstructing the 3D positions of the markers. In particular, the depth information provided by the depth frames are used for isolating a validity area within the color frames, and the markers are searched based on their colors, exclusively within the validity area of the color frames. The movements of the user are then captured as a sequence of positions of the markers. Combined use of color information and depth (Continued)

information provide a very reliable and accurate motion capture.

17 Claims, 7 Drawing Sheets

(51) Int. Cl.
```
G06T 7/70        (2017.01)
A61B 5/00        (2006.01)
G06T 7/246       (2017.01)
A61B 90/00       (2016.01)
```
(52) U.S. Cl.
CPC .......... *A61B 5/1125* (2013.01); *A61B 5/4082* (2013.01); *A61B 5/7221* (2013.01); *G06T 7/246* (2017.01); *G06T 7/70* (2017.01); *H04N 7/181* (2013.01); *A61B 2090/3937* (2016.02); *A61B 2560/0233* (2013.01); *A61B 2576/00* (2013.01); *G06T 2207/10024* (2013.01); *G06T 2207/30204* (2013.01)

(58) Field of Classification Search
USPC ........... 348/77, 159; 382/103; 600/473, 483; 345/156, 420
See application file for complete search history.

(56) References Cited

U.S. PATENT DOCUMENTS

| | | | |
|---|---|---|---|
| 8,401,225 B2 | 3/2013 | Newcombe et al. | |
| 8,718,748 B2 * | 5/2014 | Reinhold | A61B 5/1113 600/473 |
| 2011/0102570 A1 | 5/2011 | Wilf et al. | |
| 2013/0324857 A1 | 12/2013 | Kurillo et al. | |
| 2014/0276130 A1 * | 9/2014 | Mirelman | A61B 5/744 600/483 |
| 2015/0055829 A1 * | 2/2015 | Liang | G06K 9/00536 382/103 |
| 2015/0097937 A1 * | 4/2015 | Kord | G06T 7/80 348/77 |
| 2015/0213653 A1 * | 7/2015 | Kord | A63F 13/428 345/420 |
| 2017/0086712 A1 * | 3/2017 | Mauro | A61B 5/1127 |

OTHER PUBLICATIONS

K. Dere et al., "Projection and Interaction with Ad-hoc Interfaces on Non-planar Surfaces," 2013 2nd Int'l Conf. on Advanced Computing, Networking and Security, IEEE., Dec. 15, 2013, pp. 1-6, XP032551826.

Z. Ren et al., "Robust Part-Based Hand Gesture Recognition Using Kinect Sensor," IEEE Transactions on Multimedia, IEEE Service Center, vol. 15., No. 5, Aug. 1, 2013, pp. 1110-1120, XP011520563.

F. Cordella et al., "Patient Performance Evaluation Using Kinect and Monte Carlo-Based Finger Tracking," Biomedical Robotics and Biomechatronics (BIOROB), 2012 4th IEEE RAS&EMBS International Conference on, IEEE, Jun. 24, 2012, pp. 1967-1972, XP032234058.

J. Fredriksson et al., "Real-Time 3d Hand-Computer Interaction," Proc. of the 5th Nordic Conf. on Human-Computer Interaction Building Bridges, Nordichi '08, New York, NY, (Jan. 1, 2008), p. 133, XP55165560.

R. Wang et al., "Practical Color-Based Motion Capture," Mar. 10, 2011, Massachusetts Institute of Technology, XP55165566, 99 pages.

I. Oikonomidis et al., "Efficient Model-based 3D Tracking of Hand Articulations using Kinect", Proc. of BMVA'11, 2011, XP055152727.

P. Smyth et al, "Motion capture Technologies for Pose Estimation", Chapter 5 in Skill Training in Multimodal Virtual Environments, CRC Press 2012, pp. 69-80, XP055165572.

G. Placidi, "A smart virtual glove for the hand telerehabilitation", Computers in Biology and Medicine, vol. 37, Issue 8, Aug. 2007, pp. 1100-1107.

L. Lamberti et al. "Handy: A real-time three color glove-based gesture recognizer with learning vector quantization", Expert Systems with Applications, vol. 39, Issue 12, (Sep. 15, 2012), pp. 10489-10494 XP028487577.

R. Wang et al. "Real-Time Hand-Tracking with a Color Glove", Proceedings of SIGGRAPH'09, 8 pages.

L. Figuerido et al. "An open-source framework for air guitar games", Proceedings of VIII Brazilian Symposium on Games and Digital Entertainment, (Oct. 8, 2009), pp. 69-75.

G. Bradski et al. "Learning OpenCV", Sep. 2008 (First Edition), O'Reilly, pp. 153-161 and 337-341.

* cited by examiner

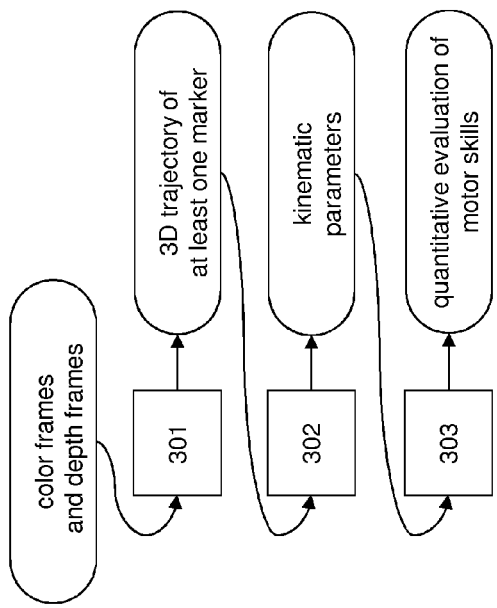
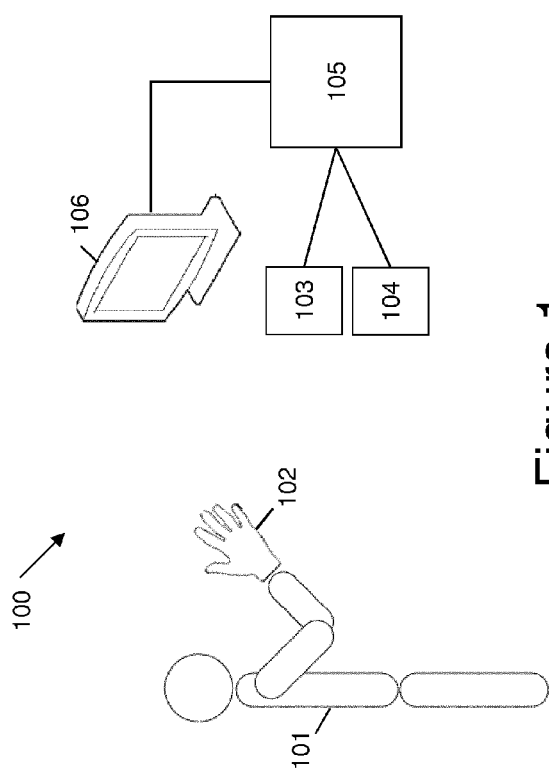

SYSTEM AND METHOD FOR MOTION CAPTURE

TECHNICAL FIELD

The present invention generally relates to the field of motion capture. In particular, the present invention relates to a system and method for capturing motion of a human body or a part thereof, especially (but not exclusively) for medical applications such as monitoring the progression of a neurodegenerative disease (e.g. Parkinson's disease, multiple sclerosis) entailing motor difficulties.

BACKGROUND ART

As known, motor difficulties (such as slowness and/or interruptions in the execution of some movements, tremors and rigidity) are amongst the main symptoms of many neurodegenerative diseases, such as the Parkinson's disease. The known Unified Parkinson's Disease Rating Scale (in brief, UPDRS) is a rating scale used to follow the progression of Parkinson's disease, which defines some standard motion exercises for upper limbs (e.g. finger tapping, hand movements, pronation-supination movements of the hands) and lower limbs of patients. The patient is periodically asked to execute these exercises under the observation of a specialized doctor who, based on her/his personal perception and experience, assigns a score to the motor skills of the patient.

Use of motion capture techniques would allow providing an objective evaluation of the motor skills of the patient, and then of the progression of the disease.

Motion capture techniques provide for digitally recording the movements of an articulated object or person, and are nowadays widespread in many fields such as military, entertainment (e.g. video-games), sports, as well as in the medical field.

Non-optical motion capture systems and optical motion capture systems are known.

Non-optical motion capture systems comprise sensors (e.g. magnetic sensors, inertial sensors, etc.), which are worn by the user and are able to transmit data detected during the user's motion to a computer. The computer, by applying suitable algorithms to the received data, extrapolates kinematic quantities of the user movements, including e.g. the amplitude of the movements, speeds and accelerations.

Optical motion capture systems, on the other hand, are based on the processing of data captured by image sensors framing the scene in which the user moves.

Optical systems may rely on markers attached to pre-defined points of the human body (typically, the joints). Basically, they reconstruct the movements of the markers in the three-dimensional space using triangulation techniques. Markerless optical systems are also known, which typically comprise range cameras, i.e. cameras capable of detecting the depth of each point of a framed scene, namely its distance from a predefined point of the scene. In order to provide depth information, range cameras exploit different principles, e.g. stereo triangulation, structured light, time-of-flight, interferometry, etc. Differently from marker-based systems, markerless systems provide spatially dense information on the user (namely, they provide the depth of every point of the user in a substantially continuous way) and his/her movements in the three-dimensional space.

Optical systems for capturing motion of a hand have also been developed, which may be either marker-based or markerless and isolate the hand from the rest of the scene based on its color.

For example, U.S. Pat. No. 6,128,003 describes a hand gesture recognition system using a colored glove. Color segmentation is used to identify hand-color regions.

G. Placidi, "A smart virtual glove for the hand telerehabilitation", Computers in Biology and Medicine, Volume 37, Issue 8, August 2007, Pages 1100-1107, describes a virtual glove, software based, which tracks hand movements by using images collected from webcams and numerical analysis.

L. Lamberti et al. "Handy: A real-time three color glove-based gesture recognizer with learning vector quantization", Expert Systems with Applications, Volume 39, Issue 12, 15 Sep. 2012, Pages 10489-10494 describes a real-time hand gesture recognizer based on a three color glove. The recognizer, fed by the frame acquired by a webcam, identifies the hand image in the scene.

Robert Y. Wang et al. "Real-Time Hand-Tracking with a Color Glove", Proceedings of SIGGRAPH'09 describes a hand-tracking system using a single webcam to track a hand wearing an ordinary cloth glove that is imprinted with a custom pattern. The pattern is designed to allow use of a nearest-neighbour approach to track hands at interactive rates.

L. Figuerido et al. "An open-source framework for air guitar games", Proceedings of VIII Brazilian Symposium on Games and Digital Entertainment, Oct. 8th-10th 2009, discloses a system for tracking the player's hand using a color tracking approach based on a webcam and a pair of yellow gloves to be worn by the player.

Markerless optical systems for capturing motion of a hand based on range cameras have also been developed, which isolate the hand from the rest of the scene based on depth information.

For example, US 2011/102570 describes a man machine interface assisted with computer vision, e.g. for tracking movements of hands above a keyboard, where three dimensional tracking is provided by two or more cameras providing stereoscopic imaging of the hands above the keyboard.

U.S. Pat. No. 7,372,977 describes a system for real-time visual tracking using depth sensing (time-of-flight) camera technology, results in illumination-invariant tracking performance.

Kinect® sensor developed by Microsoft typically includes a range camera built in with a RGB camera and a microchip capable of tracking the movement of objects and individuals in three dimensions employing a variant of image-based 3D reconstruction using the depth information provided by the range camera. The range camera consists of an infrared laser projector combined with a monochrome CMOS sensor.

I. Oikonomidis et al. "Efficient Model-based 3D Tracking of Hand Articulations using Kinect", Proceedings of BMVA'11 describes a system for recovering and tracking the 3D position, orientation and full articulation of a human hand from markerless visual observations obtained by a Kinect® sensor, seeking for hand model parameters that minimize the discrepancy between the appearance and 3D structure of hypothesized instances of a hand model and actual hand observations.

WO 2013/109608 and WO 2013/109609 relate to the known Leap Motion® controller, which is a USB peripheral device designed to be placed on a physical desktop. It comprises two monochromatic IR cameras and three infrared LEDs. The LEDs generate a 3D pattern of dots of IR light and the cameras generate respective 2D frames, which are then sent to the host computer, where they are analyzed by the Leap Motion controller software so as to synthesize 3D position data by comparing the 2D frames generated by the two cameras.

U.S. Pat. No. 8,401,225 describes a moving object segmentation using depth images. A moving object is segmented from the background of a depth image of a scene received from a mobile depth camera. A previous depth image of the scene is retrieved, and compared to the current depth image using an iterative closest point algorithm. The iterative closest point algorithm includes a determination of a set of points that correspond between the current depth image and the previous depth image. During the determination of the set of points, one or more outlying points are detected that do not correspond between the two depth images, and the image elements at these outlying points are labeled as belonging to the moving object.

SUMMARY OF THE INVENTION

The inventors have noticed that the above known motion capture systems are not suitable for providing an evaluation of the motor skills of a user and in particular of the progression of a neurodegenerative disease entailing motor difficulties as one of the main symptoms.

As to non-optical systems, the sensors may disadvantageously hamper the natural movements of the user, thereby altering the results of the motion test, especially on small articulated body parts such as the hands. Furthermore, the sensors shall be positioned by a skilled operator, thereby preventing such systems from being used by users in an autonomous way.

Similar considerations apply to marker-based optical systems.

As to the markerless optical systems, in principle they do not suffer from the above drawbacks, in that the user does not have to wear any sensor or marker. However, many of such systems are mainly developed for gaming applications, where accuracy requirements are much more relaxed than those needed for the above mentioned medical application.

As to the systems specifically developed for capturing motion of a hand, those that make use of one or more webcams (e.g. standard RGB cameras) with or without a colored glove, they have difficulties in isolating the hand from the rest of the framed scene, though use of the colored glove in part relieves this issue. Besides, they exhibit a limited accuracy in reconstructing the hand movements, because they basically reconstruct the hand movements by comparing the reconstructed hand positions with a set of known predefined hand positions ("training set"). Intermediate positions not included in the training set may be interpolated starting from the predefined hand positions of the training set, but the result is not accurate. Furthermore, since in such systems the isolation of the hand from the rest of the scene is mainly based on a color identification technique, the illumination of the scene may strongly affect the way in which colors are perceived by the webcam(s), and may accordingly affect the capability of the system to properly isolate the hand.

As to markerless systems specifically developed for capturing motion of a hand and making use of range cameras, in principle a range camera may properly isolate the hand from the rest of the scene independently of the illumination conditions, the isolation of the hand being based on its distance from the camera and not on identification of its color. However, such systems exhibit other drawbacks.

Generally, the tracking of the hand starting from depth information may be based on an appearance-based approach or a model-based approach.

As to the appearance-based approach (used e.g. by Kinect®), it disadvantageously does not allow to track body movements with the accuracy required for the above cited medical application, especially on small articulated body parts such as the hands.

On the other hand, the model-based approach (used e.g. by I. Oikonomidis et al. "Efficient Model-based 3D Tracking of Hand Articulations using Kinect") is more accurate but it requires a very large computational effort and is therefore difficult to implement for a real-time analysis of the acquired images.

Furthermore, the system described by US 2011/102570 is capable to recognize only some specific fixed hand postures on the keyboard, and not to capture the tridimensional movements of the hands (or other parts of the body).

As to Leap Motion®, the reconstructed positions of the fingers largely depend on the hand orientation, thereby making the results not very reliable. Moreover, Leap Motion® is specifically designed to capture motion of hands confined within a small size volume (typically 50×50×50 cm), and accordingly this device cannot be used to capture movements of parts of the body.

As to the system described by U.S. Pat. No. 8,401,225, its algorithm is complex since it identifies the points of the object of interest based on the comparison between two consecutive frames. This may make this system unsuitable for providing a real-time analysis of the movements, unless a processor with a very high computational capacity (and hence a very high cost) is used. Further, this system is specifically configured to recognized static or moving objects entering and exiting a scene by analyzing time variations of the depth of pixels. This approach may be not effective for capturing the motion of an object (e.g. a hand) which is persistently present in the scene.

In view of the above, the inventors have tackled the problem of providing a motion capture system suitable for providing a quantitative and objective evaluation of the motor skills of a user (in particular, but not exclusively, of her/his hand), and therefore—for example—of the progression of a neurodegenerative disease entailing motor difficulties as one of the main symptoms.

In particular, the inventors have tackled the problem of providing a motion capture system and method which is capable to perform a real-time tracking of the movements of a user with an accuracy sufficient to enable the extrapolation of kinematic quantities of the movements (including e.g. the range of the movements, velocity, acceleration, frequency, etc.). Possibility of an autonomous use of the system by the user and low cost are also desirable features of the system.

According to the present invention, the above problems are solved by a motion capture system that comprises a wearable device (e.g. a glove) suitable for being worn by a user and comprising one or more markers having respective colors. The system comprises a video camera that acquires a sequence of color frames of the user moving while wearing the glove, and range camera that, at the same time, acquires corresponding depth frames of the same scene. The system also comprises a processing unit, which processes both color frames and depth frames for reconstructing the three-dimensional positions of the markers. In particular, the depth information provided by the depth frames are used for isolating a validity area within the color frames, and the markers are searched based on their colors, exclusively within the validity area of the color frames. Combined use of color information and depth information provide a very reliable and accurate tracking of the movements of the user.

According to a first aspect, the present invention provides a motion capture system comprising:
- a wearable device suitable for being fitted on at least part of the body of a user, the wearable device comprising at least one marker having a predetermined marker color;
- a video camera suitable for acquiring at least one color frame of a scene comprising the wearable device, the at least one marker being visible in the at least one color frame;
- a range camera suitable for acquiring at least one depth frame of the scene; and
- a processing unit configured to receive the at least one color frame from the video camera and the at least one depth frame from the range camera, to process the at least one depth frame for identifying in the at least one color frame a validity area comprising pixels representing the wearable device, to search the at least one marker in the at least one color frame based on the marker color, the search being confined in the validity area, and to capture a motion of the part of the body of the user on the basis of a sequence of positions of the at least one marker.

Preferably, the wearable device is made of a flexible and opaque material.

According to particularly preferred variants, the material of the wearable device is a fabric.

Preferably, the wearable device has an external surface of a background color different from the marker color.

Preferably, the wearable device comprises at least two markers, the at least two markers comprising a color calibration marker whose marker color is white.

According to particularly preferred variants, the color calibration marker is a circular marker.

Preferably, the at least two markers comprise at least one further marker other than the color calibration marker, having a marker color different from white. The marker colors are preferably as separated as possible within a selected color space.

Preferably, the at least one marker is made of a piece of a flexible material fixed to an external surface of the wearable device.

Alternatively, the at least one marker is painted on an external surface of the wearable device.

According to a preferred variant, the video camera and the range camera are integrated within a same device.

Further, according to a preferred variant, the video camera is configured to provide the at least one color frame in the form of a matrix of pixels, each pixel having associated a tuple of color components defining the pixel color within a predefined color space. Further, the range camera is preferably configured to provide the at least one depth frame in the form of a further matrix of pixels, each pixel having associated a numerical value indicating a depth of the pixel.

Preferably, the at least one color frame and the at least one depth frame have a same size of N×M pixels.

Preferably, the video camera and the range camera are synchronized so as to acquire the at least one color frame and the at least one depth frame substantially at the same time.

Preferably, the system further comprises a display connected to the processing unit and configured to display a graphic user interface suitable for enabling interaction between the user and the processing unit.

Optionally, the graphic user interface is suitable for providing indications to the user by using augmented reality techniques.

According to preferred embodiments, the processing unit is configured to perform a brightness calibration, before searching the at least one marker in the at least one color frame, the brightness calibration comprising adjusting a gain of the video camera so as to bring an average brightness of the at least one color frame within a predefined range.

In particular, the processing unit is preferably configured to perform the brightness calibration by setting the gain of the video camera to an initial value before starting acquiring the at least one color frame and, upon acquisition of each color frame, calculating an average brightness of the color frame, checking whether the average brightness is comprised within the predefined range and, in the negative, adjusting the gain according to a negative feedback mechanism.

Preferably, the processing unit is configured to iterate the acquiring, checking and adjusting until either the average brightness reaches the predefined range, or a predefined number of iterations have been made.

Preferably, the processing unit is configured to determine the validity area in the at least one color frame by:
- identifying the color calibration marker in the at least one color frame, based on its shape;
- determining a two-dimensional position of a center of the color calibration marker in the at least one color frame and a depth of the center of the color calibration marker in the at least one depth frame;
- identifying in the at least one depth frame a cluster of pixels whose depth is substantially the same as the depth of the center of the color calibration marker and determining a centroid of the cluster;
- constructing a segmentation solid around the centroid of the cluster, the segmentation solid having shape and size suitable for containing the wearable device when fitted on at least part of the body of the user, independently of the current position of the at least part of the body of the user; and
- determining the validity area in the at least one color frame as a portion of the color frame formed by pixels included in the segmentation solid.

According to a preferred variant, the segmentation solid is a parallelepiped.

According to preferred embodiments, the processing unit is configured to perform a color calibration, before searching the at least one marker in the at least one color frame, the color calibration comprising calculating one or more color correction factors to be applied to the at least one color frame and/or selecting a set of color thresholds to be used for searching the at least one marker in the validity area of the at least one color frame.

According to preferred embodiments, the processing unit is configured to calculate the one or more color correction factors by:
- identifying the color calibration marker in the at least one color frame, based on its shape;
- calculating average color components of a portion of the color calibration marker; and
- calculating the one or more color correction factors to be applied to the at least one color frame based on the average color components of the portion of the color calibration marker.

According to preferred embodiments, the processing unit is configured to select the set of color thresholds to be used for searching the at least one marker in the validity area of the at least one color frame by:
  identifying the calibration marker in the color frame, based on its shape;
  calculating an average brightness of a portion of the color calibration marker; and
  selecting the set of color thresholds based on the average brightness of the portion of the color calibration marker.

Preferably, the processing unit is configured to apply the one or more color correction factors only to the validity area of the at least one color frame, before searching the at least one marker in the validity area of the at least one color frame.

According to a preferred variant, before searching the at least one marker in the at least one color frame, the processing unit is further configured to apply a transformation into a hue saturation value (HSV) color space to the at least one color frame.

Preferably, the processing unit is configured to search the at least one marker in the validity area of the at least one color frame by identifying, within the validity area of the at least one color frame, at least one marker color blob formed by contiguous pixels having the marker color.

Preferably, the processing unit is configured to identify the at least one marker color blob by comparing color components of each pixel of the validity area with the set of color thresholds selected during the color calibration.

Preferably, the processing unit is further configured to determine a three-dimensional position of the at least one marker by processing both the at least one color frame and the at least one depth frame.

In particular, the processing unit is preferably configured to determine the three-dimensional position of the at least one marker by:
  determining a two-dimensional position of a center of the at least one marker color blob in the at least one color frame;
  determining a pseudo-three dimensional position of the at least one marker, the pseudo-three dimensional position comprising the two-dimensional position of the center of the at least one marker color blob in the at least one color frame and a depth of the center of the at least one marker color blob in the at least one depth frame; and
  converting the pseudo-three dimensional position of the at least one marker into a tern of coordinates that indicate the three dimensional position of the at least one marker relative to a Cartesian coordinate system.

Preferably, the processing unit is further configured to refine the validity area of the at least one color frame using color information.

In particular, the processing unit is preferably configured to refine the validity area of the at least one color frame by:
  identifying, within the validity area of the at least one color frame, at least one marker color blob formed by contiguous pixels having the marker color;
  identifying, within the validity area of the at least one color frame, a background color blob formed by contiguous pixels having the background color;
  calculating a separate color histogram for each one of the at least one marker color blob and the background color blob;
  calculating a cumulative color histogram by merging the separate color histograms for the at least one marker color blob and the background color blob; and
  refining the validity area of the at least one color frame by excluding from the validity area those pixels whose probability of belonging to the cumulative color histogram is substantially null.

According to a preferred variant, the system further comprises a memory device, the processing unit being configured to store the three-dimensional position of the at least one marker in the memory device.

Preferably, the processing unit is configured to determine a sequence of three-dimensional positions of the at least one marker and to calculate a three-dimensional trajectory of the at least one marker as the sequence of three-dimensional positions of the at least one marker.

Preferably, the processing unit is further configured to process the three-dimensional trajectory of the at least one marker for calculating one or more kinematic quantities relating to the movement of the part of the body of the user, the one or more kinematic quantities including one or more of: movement range, movement velocity, movement acceleration, movement frequency.

Preferably, the processing unit is further configured to provide a quantitative evaluation of the motor skills of the user on the basis of the one or more calculated kinematic quantities.

According to a second aspect, the present invention provides a method for capturing motion of at least part of the body of a user upon which a wearable device is fitted, the wearable device comprising at least one marker having a predetermined marker color, the method comprising:
a) receiving, from a video camera, at least one color frame of a scene comprising the wearable device, the at least one marker being visible in the at least one color frame;
b) receiving, from a range camera, at least one depth frame of the scene;
c) processing the at least one depth frame for identifying in the at least one color frame a validity area comprising pixels representing the wearable device;
d) searching the at least one marker in the at least one color frame based on the marker color, the search being confined in the validity area; and
e) capturing a motion of the part of the body of the user on the basis of a sequence of positions of the at least one marker.

According to a third aspect, the present invention provides a computer program product loadable in the memory of at least one computer and including software code portions for performing the steps of the method as set forth above, when the product is run on the at least one computer.

BRIEF DESCRIPTION OF THE DRAWINGS

The present invention will become clearer from the following detailed description, given by way of example and not of limitation, to be read with reference to the accompanying drawings, wherein:
FIG. 1 schematically shows a motion capture system according to an embodiment of the present invention;
FIG. 3 is a block diagram of the program software executed by the processing unit of the system of FIG. 1.

DETAILED DESCRIPTION OF PREFERRED EMBODIMENTS OF THE INVENTION

Figure 2B:
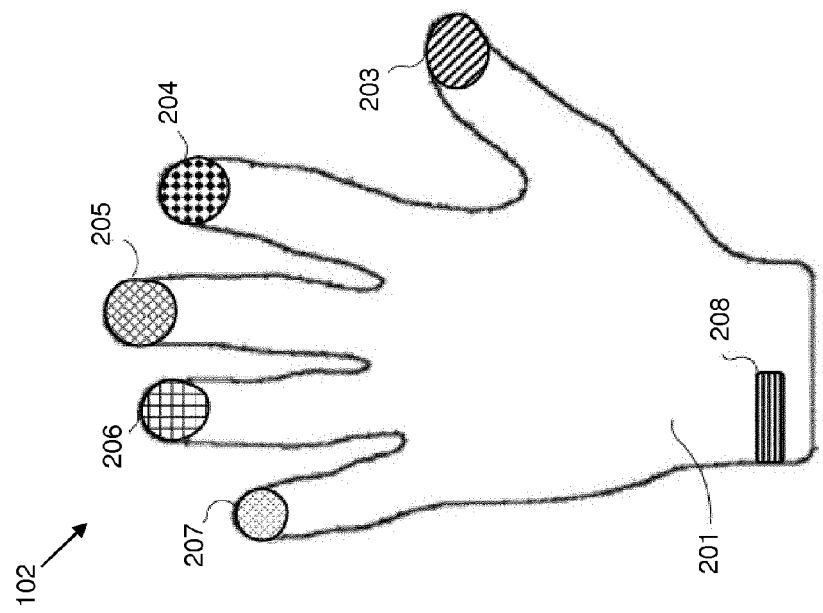
FIGS. 2a and 2b show palmar side and dorsal side, respectively, of a wearable device in the form of a glove, according to an embodiment of the present invention.

With reference to FIG. 1, a motion capture system 100 according to an embodiment of the present invention will be described in detail.

The motion capture system 100 preferably comprises a wearable device 102 suitable for being worn by a user 101 on the part of his/her body whose motion has to be captured. By way of non limiting example, it is assumed hereinafter that the motion of a hand of the user 101 has to be captured. The wearable device 102 is accordingly in the form of a glove provided with at least one marker applied to its external surface 201

Preferably, the motion capture system 100 comprises a video camera 103, a range camera 104 and a processing unit 105.

The video camera 103 is preferably configured to provide a sequence of color frames of a scene in which the user 101 wearing the wearable device 102 is moving. Each color frame is preferably in the form of a matrix of N×M pixels, each pixel having associated a tuple (typically, a tern) of color components defining the pixel color. According to preferred embodiments, the video camera 103 is a RGB (Red Green Blue) camera, which provides, for each pixel, the RGB components of the pixel color.

The range camera 104 is preferably configured to provide a sequence of depth frames of the same scene framed by the video camera 103. Each depth frame (or "depth map") is preferably in the form of a matrix of N×M pixels, each pixel having associated a numerical value indicating the distance of the point represented by the pixel from a certain predefined point (e.g. expressed in mm). The predefined point from which distances are measured depends on the type of range camera, which may be a structured light range camera, a time-of-flight range camera, etc. In the following description and in the claims, the distance between a point of the scene and such predefined point as detected by the range camera 104 will be named as "depth".

Preferably, the color frames acquired by the video camera 103 and the depth frames acquired by the range camera 104 have the same size N×M, meaning that a one-to-one correspondence exists between pixels of the color frames and pixels of the depth frames.

According to preferred embodiments, the video camera 103 and the range camera 104 are integrated within a same device (also named as "3D camera"). This is advantageous in terms of size reduction. The inventors have made positive tests using a Microsoft Kinect® device that, as known, integrates a RGB camera and a structured light range camera and provides RGB frames and depth frames of 640×480 pixels each, at a frame rate of 30 fps.

The processing unit 105 is preferably connected to both the video camera 103 and the range camera 104. The processing unit 105 is configured to receive the sequence of color frames acquired by the video camera 103 and the sequence of depth frames acquired by the range camera 104, and to process them for capturing the movements of the body portion of the user 101 covered by the wearable device 102, as it will be described in detail hereinafter. The processing unit 105 preferably is a PC.

Preferably, the motion capture system 100 comprises a display 106 connected to the processing unit 105. The display 106 is preferably configured to display a graphic user interface suitable for enabling interaction between the user 101 and the processing unit 105. Preferably, the graphic user interface provides indications to the user 101 by using augmented reality techniques, namely by displaying one or more graphical objects (text portions, labels, arrows, etc.) superimposed to the live scene shown by the display 106. The graphic user interface may comprise menus for selecting motor exercises to be performed by the user 101 and instructions for guiding the user step-by-step through the various phases of a motion capturing session (e.g. the color calibration step, that will be described in detail hereinafter). The display 106 may also be configured to display one or more tutorial videos illustrating to the user 101 the selected motor exercise(s).

The system 100 may also be provided with an audio device suitable for playing voice instructions, e.g. for integrating the textual and/or graphical instructions provided via the display 106.

It shall be noticed that no input peripherals (e.g. mouse, keyboard, etc.) are needed, because the system 100 is inherently capable of recognizing the movements of the hand of the user 101, which accordingly acts as a virtual mouse to impart commands to the system 100.

Figure 2A:
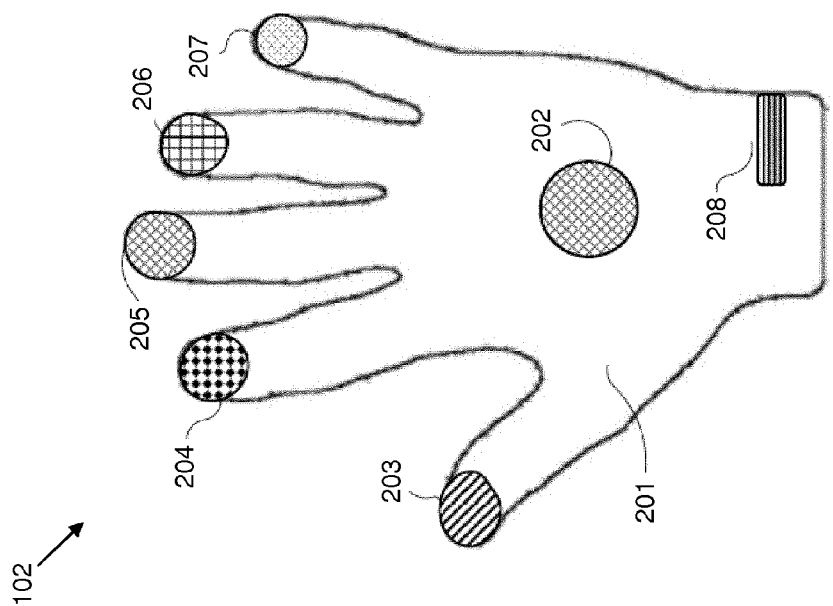

With reference now to FIGS. 2a and 2b, the wearable device 102 (which, as discussed above, in the embodiment herein described is a glove) is preferably made of a thin, light and flexible material, so as to adhere to the body of the user 101 and not to hamper his/her natural movements. The material of the wearable device 102 is preferably an opaque material. According to preferred embodiments, the wearable device 102 is made of a thin fabric. The external surface 201 of the wearable device 102 is preferably of a first color (also named hereinafter as "background color"). The background color is preferably selected so as to ease the identification of the wearable device 102 within the scene framed by the video camera 103. To this purpose, the background color is preferably a color which is rarely present in real domestic environments, e.g. black. The background color is also preferably selected so as to maximize the contrast with the colors of the markers applied to the external surface 201 of the wearable device 102.

Preferably, the external surface 201 of the wearable device 102 is provided with at least one marker, namely an area having a certain shape and being colored by a second color different from the first, background color of the wearable device 102.

The number of markers and their positions depend on the types of movements that shall be captured. For instance, if one wishes to capture the movements of all the fingers of a hand and wrist rotation movements, the following markers are preferably provided:

- a first marker 202 positioned at the center of the palm (see FIG. 2a), whose function is also to ease calibration of the system 100, as it will be described hereinafter;
- at least one second marker for each fingertip whose movement shall be captured. The glove 102 shown in FIGS. 2a and 2b comprises five second markers 203, 204, 205, 206, 207, each one being positioned at a respective fingertip, thereby allowing movements of all the fingers of the hand to be captured; and
- a third marker 208 positioned at the wrist.

The shape of each marker depends on the function that it carries out. As to the first marker 202, it is preferably circular, so as to ease its identification based on recognition of its shape during a segmentation step, as it will be discussed in detail hereinafter. As to the second markers 203, 204, 205, 206, 207, each of them preferably covers the respective fingertip on both the palmar side (shown in FIG. 2a) and the dorsal side (shown in FIG. 2b) of the glove 102, in order to maximize the visibility of the fingertip during its motion. As to the third marker 208, it is preferably in the form of a strip that partially surrounds the external side of the wrist, so as to be visible both on the palmar side and the dorsal side of the glove 102. This eases recognition of wrist rotation movements.

Also the color of each marker depends on the function that it carries out. As to the first marker 202, it is preferably white, so as to enable a color calibration step, as it will be discussed in detail hereinafter. Alternatively, a color different from white may be used for the first marker 202, provided that the hue of the marker color is selected so as to include a non negligible component of each of the elementary hues detected by the video camera 103, so that color calibration is possible by evaluation of the actual color component values detected for the marker 202 by the video camera 103 under the light that lightens the scene. As to the second markers 203, 204, 205, 206, 207, since their function is allowing the movements of each single fingertip to be captured, their colors are preferably selected so as to ease distinguishing each marker from the other ones based on its color. Hence, the colors of the second markers 203, 204, 205, 206, 207 are preferably as separated as possible within the color space selected for representing the pixel colors (e.g. yellow, green, red, blue, light blue). As to the third marker 208, it is preferably a bicolor strip, the dorsal-side portion of the strip being of a certain color (e.g. white) and the palm-side portion of the strip being of a different color (e.g. orange). This eases distinguishing the palm side and the dorsal side of the glove 102.

The markers 202, 203, 204, 205, 206, 207, 208 may be either pieces of a light, thin, flexible and colored material, which are fixed (e.g. stitched or glued) to the external surface 201 of the wearable device 102. Alternatively, the markers 202, 203, 204, 205, 206, 207, 208 may be painted on the external surface 201 of the wearable device 102 by using suitable colored paints for tissues.

Since, when the user 101 wears the wearable device 102, each marker 202, 203, 204, 205, 206, 207, 208 is bounded to a certain position of her/his hand, capturing movements of the markers 202, 203, 204, 205, 206, 207, 208 basically amounts to capturing the movements of the hand of the user 101.

The logical structure and operation of the processing unit 105 for capturing the movements of the markers of the wearable device 102 will be now described in detail.

With reference to FIG. 3, the processing unit 105 is preferably configured to execute a software program that comprises three logically-interrelated functional blocks.

A first block 301 is configured to acquire the color frames and range frames provided by the video camera 103 and range camera 104, respectively, and processes them for calculating the three-dimensional trajectory of at least one marker of the wearable device 102. The three-dimensional trajectory of a marker basically is a sequence of positions that the marker assumes in the three-dimensional space over time.

A second block 302 is preferably configured to receive the three-dimensional trajectories of the markers and process them for calculating one or more kinematic quantities (e.g. range, speed, acceleration, rate, frequency, etc.) relating to the movements of the user 101, as it will be described in detail hereinafter.

A third block 303 is preferably configured to receive the one or more kinematic quantities and to process them for providing a quantitative evaluation of the motor skills of the user 101 and, possibly, of the progression of a neurodegenerative disease (e.g. Parkinson's disease) in the user 101. Also this block will be described in detail hereinafter.

Figure 4:
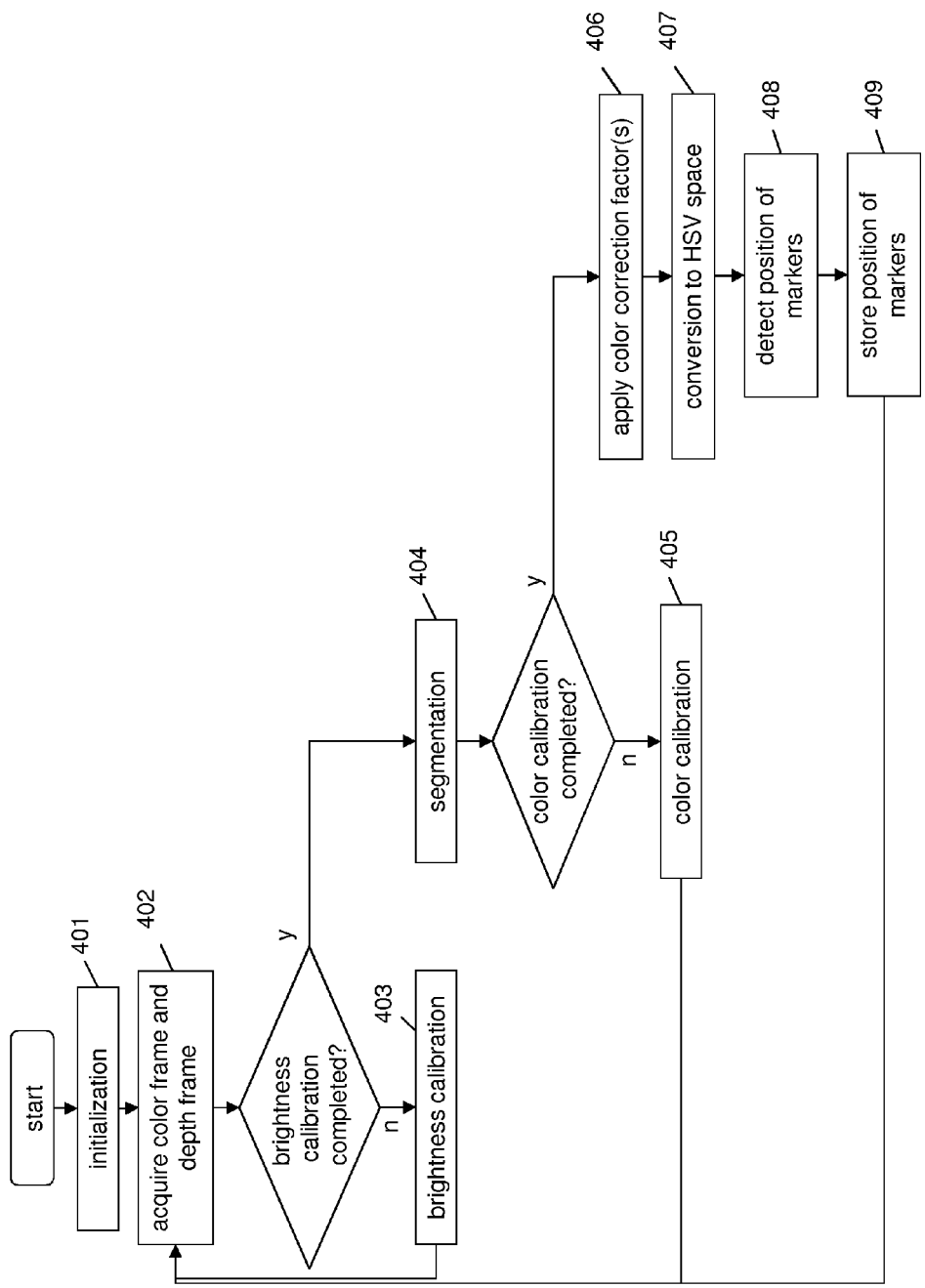
FIG. 4 is a flow chart of the operation of the first block of FIG. 3.

The operation of the processing unit 105 when it executes the first block 301 of the software program will be now described in detail, with reference to the flow chart of FIG. 4.

When the user 101 wishes to start a motion capturing session, he/she preferably wears the wearable device 102 and switches on the processing unit 105, that firstly performs an initialization step 401.

During the initialization step 401, the processing unit 105 preferably loads a set of configuration parameters (e.g. contained in a XML configuration file stored in a memory unit of the processor unit 105) that comprise parameters for customizing the system 100. Such configuration parameters preferably comprise one or more of the following ones:

parameters for customizing the graphical user interface shown by the display 106, e.g. by enabling or disabling visualization of a window that shows in real time the calculated three-dimensional trajectories of the markers or of a window that shows the live image of the user 101 as captured by the video camera 103;

parameters for customizing the information to be stored, such as: enabling or disabling storing of personal records of the user 101 and selection of the information to be recorded therein, enabling or disabling recording of a video during execution of motor exercises by the user 101, enabling or disabling storing of the windows showing in real time the calculated three-dimensional trajectories of the markers, etc.;

parameters for setting the features of the motor exercise(s) to be executed by the user 101, e.g. time-based execution (with customization of the maximum time for executing an exercise) or event-based execution (with customization of the number of iterations of a certain movement within an exercise);

parameters allowing to set a "guided mode" by means of which the system 100 guides the user 101 in the execution of a predefined sequence of exercises, with the possibility to customize the number of iterations of each exercise; and parameters allowing to choose one or more motor exercises.

Besides, during the initialization step 401, the processing unit 105 preferably activates a communication session with the video camera 103 and the range camera 104. At the initialization step 401, preferably, the processing unit 105 also disables the auto-exposure mode of the video camera 103 (if present), namely the mode in which the video camera 103 automatically adjusts the amount of light entering the camera's objective. Further, preferably, the processing unit 105 also enables the anti-flicker filter of the video camera 103 (if present), namely the filter that filters out the "flickering" of the acquired images due to intensity oscillations of light emitted by some types of artificial light sources (e.g. neon lightings). Further, preferably, the processing unit 105 enables the near-mode function of the video camera 103 (if present), that allows the video camera 103 to be more sensitive and accurate to closer objects. In order to perform such steps, according to an embodiment of the present invention, the processing unit 105 makes use of software modules of the OpenNI libraries.

As the initialization step 401 is completed, the processing unit 105 starts receiving color frames from the video camera 103 and depth frames from the range camera 104 (step 402). Preferably, acquisition of color frames and acquisition of depth frames are reciprocally synchronized, meaning that when a color frame is acquired, at the same time also a depth frame is acquired. This guarantees that each color frame is biuniquely associated to a depth frame referring to the same scene and captured substantially at the same moment.

Then, the processing unit 105 preferably performs a brightness calibration step 403. As it will be described in detail hereinafter, according to the present invention, the recognition of the markers of the wearable device 102 in order to capture their movements is based on a color recognition technique. This means that the markers are recognized based on their color, which requires comparing their color components (e.g. in the RGB space or the HSV space) as provided by the video camera 103 with a set of predefined color thresholds, that define an upper and lower limit for each color component. Variations in the lighting conditions of the environment (which may be lightened either by artificial light or natural light) affect the way the video camera 103 perceives the colors of the environment, and in particular of the markers. This may impair the proper recognition of the markers based on their colors. In order to compensate this drawback, the processing unit 105 preferably performs the brightness calibration step 403 that— together with a subsequent color calibration step, which will be described hereinafter—allows adjusting the operation of the system 100 to the actual lightning conditions of the environment, thereby allowing the system 100 to properly recognize the markers based on their colors independently of the lighting conditions.

More particularly, after disabling the auto-exposure mode (if present) at the preceding step 401, at step 403 the processing unit 105 adjusts the gain of the video camera 103 so as to bring the average brightness of the acquired color frame within a certain predefined range. The inventors have made positive tests using a brightness range of 160 to 180. This brightness range provides color frames with pixels whose color components have values substantially comprised between ½ and ¾ of the maximum value that each color component may assume (namely, 255). It should be noted that in a Kinect® device, the gain of the color camera (e.g. a RGB camera) is a magnification factor by which the color components of each pixel of a color frame are multiplied in order to adjust the brightness of the color frame provided by the camera.

Specifically, before starting acquiring color frames from the video camera 103, the processing unit 105 sets the gain of the video camera 103 to an initial value. Preferably, since the gain may typically range between a minimum value (e.g. 1 in Kinect®) and a maximum value (e.g. 16 in Kinect®), the initial value is set equal to the average value of the range.

Then, upon reception of the first color frame, at step 403 the processing unit 105 preferably calculates its average brightness, checks whether it is comprised within the desired predefined brightness range and, in the negative, via software adjusts the gain value according to a negative feedback mechanism (namely, it increases the gain if the average brightness is too low or decreases the gain if the average brightness is too high). Then, the processing unit 105 receives the subsequent color frame from the video camera 103 and repeats step 403, namely calculates the average brightness of the acquired color frame, checks whether it is comprised within the desired predefined range and, in the negative, adjusts again the gain value of the video camera according to the negative feedback mechanism.

Steps 402-403 are repeated until brightness calibration is completed, namely until either the average brightness reaches the desired range, or a predefined number of iterations of steps 402-403 have been made. The inventors have estimated that, typically, 50 iterations of steps 402-403 are sufficient to bring the average brightness to the desired range, namely the brightness calibration is generally completed upon acquisition of the first 50 color frames. Assuming that the frame rate of the video camera 103 is 30 fps, it follows that brightness calibration of system 100 advantageously takes a very short period (few seconds). Moreover, it is automatically performed by the system 100, without requiring any action by the user 101.

When brightness calibration is completed, the processing unit 105 preferably asks the user 101 to position his/her hand covered by the wearable device 102 in a predefined initial position (e.g. outstretched position with fingers pointing upwards), so that the marker 202 located at the center of the palm lies in front of the video camera 103 (step not shown in FIG. 4). To this purpose, according to embodiments of the present invention the processing unit 105 displays, by means of the display 106, the live scene framed by the video camera 103 and a target in the form of a graphical object (e.g. a circle) superimposed to the live scene, that indicates the position at which the marker 202 should be brought.

After completion of the brightness calibration, upon reception of the subsequent color frame and depth frame (step 402), the processing unit 105 carries out a segmentation step 404, during which the hand of the user 101 (or, generally, any part of the body of the user 101 which is covered by the wearable device 102) is isolated from the rest of the scene, which might include colored items hampering the proper color-based recognition of the markers.

Figure 5:
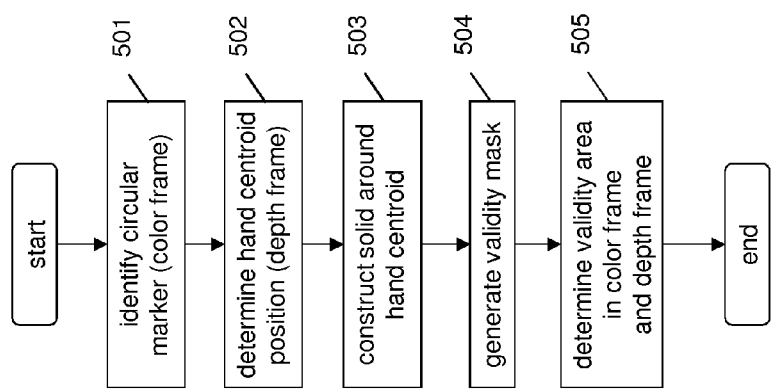

The segmentation step 404 will be described in detail hereinafter, with reference to the flow chart of FIG. 5.

At a first sub-step 501, the processing unit 105 preferably processes the color frame provided by the video camera 103 while the user 101 is holding his/her hand in the predefined initial position, in order to identify the marker 202. The processing unit 105 preferably identifies the marker 202 based on its shape and not based on its color, the latter approach being likely ineffective at this stage of the algorithm because the above mentioned color calibration (which will be described in detail hereinafter) has not been performed yet. Identification of the marker 202 based on its shape may instead be carried out properly at this stage of the algorithm, independently of the lightning conditions of the environment surrounding the system 100. Sub-step 501 is preferably carried out by applying a computer vision technique to the portion of color frame that lies within the target visualized on the display 106. According to a particularly preferred embodiment, the processing unit 105 can apply the modified Hough Transform technique described by G. Bradski et al. "Learning OpenCV", September 2008 (First Edition), O'Reilly, pages 153-161 for the recognition of circles in a digital image. The circular shape of the marker 202 advantageously eases this operation. The two-dimensional position of the center of the marker 202 is then determined. The two-dimensional position of the center of the marker 202 is preferably expressed as the row number and the column number of the pixel that, in the N×M color frame, corresponds to the center of the marker 202. Such two-dimensional position is used by the processing unit 105 as a rough initial position of the hand.

Then, at a subsequent sub-step 502, the processing unit 105 preferably "refines" the rough initial position of the hand provided at the preceding sub-step 501 by determining a refined three-dimensional position of the centroid of the hand. To this purpose, the processing unit 105 preferably reads, in the depth frame corresponding to the color frame used at sub-step 501, the depth associated to the center of the marker 202. Since, as discussed above, color frame and depth frame have the same size N×M, the depth associated to the center of the marker 202 may be easily identified within the depth frame as the depth associated to the pixel that in the N×M depth frame is located at the same row number and column number as the pixel that in the N×M color frame corresponds to the center of the marker 202. Then, a cluster of pixels is preferably identified within the depth frame, whose depth is substantially the same as the depth associated to the pixel corresponding to the center of the marker 202. To this purpose, the processing unit 105 preferably includes in the cluster all the pixels whose associated depths differ from the depth of the center of the marker 202 at most by a certain amount, which is positive for pixels farther than the center of the marker 202 from the range camera 104, and negative for pixels closer than the center of the marker 202 to the range camera 104. This amount is preferably larger than the half the typical thickness of a hand (namely, the distance between palm and dorsal area of the hand in an open-hand position).

The three-dimensional position of each pixel of the cluster is described by its position in terms of row number and column number within the depth frame and by the related depth. In order to identify the cluster of pixels, according to a preferred embodiment of the invention, the processing unit 105 preferably makes use of software modules of the OpenNI libraries.

After having identified the three-dimensional position of each pixel of the cluster, the processing unit 105 preferably determines a centroid of the cluster (namely, its coordinates in the three-dimensional space). If a Kinect® device is used for implementing the video camera 103 and the range camera 104, the centroid of the cluster may be determined, for instance, using a software module of the OpenNI libraries.

Then, at a sub-step 503, the processing unit 105 preferably constructs a segmentation solid around the centroid determined at sub-step 502, whose shape and size are such to contain the whole hand (or, more generally, the whole body portion whose movements shall be captured), independently of its current position or orientation. According to a preferred embodiment, the segmentation solid is a parallelepiped having predefined size and orientation within the three-dimensional coordinate system of the range camera 104. Size and orientation of the parallelepiped are preferably the same at all iterations of step 404. In particular, height and width of the parallelepiped (namely, the sizes of the parallelepiped in the plane perpendicular to the direction of the depth detected by the range camera 104) are preferably selected so as to contain the whole hand in its initial outstretched position, which is its "maximum extension" position. The depth of the parallelepiped is instead selected so as to contain the hand during movements which may for instance bring the hand into "tilted" positions (wherein e.g. the fingers are closer to the range camera 104 than the wrist). Specifically, along its depth, the parallelepiped is preferably centered in the centroid determined at sub-step 502. Along the vertical direction in the plane perpendicular to the direction of the depth detected by the range camera 104 (namely the height of the parallelepiped), the parallelepiped is shifted upwards relative to the centroid, namely towards the fingertips when the hand is held in the initial position (outstretch with fingers pointing upwards), so as to guarantee that the fingers are included in the parallelepiped. Along the horizontal direction in the plane perpendicular to the direction of the depth detected by the range camera 104 (namely the width of the parallelepiped), the parallelepiped is preferably shifted—relative to the centroid—towards the thumb when the hand is held in the initial position (outstretch with fingers pointing upwards), the thumb generally protruding more than the fourth finger. For instance, the parallelepiped may be 22 (width)×21 (height)×26 cm (depth). These exemplary sizes are larger than those strictly required for containing the hand, however they guarantee that no parts of the hand (e.g. the finger tips) are excluded from the parallelepiped, even with a very large hand and/or a tilted hand. On the other hand, these exemplary sizes likely entails the inclusion in the parallelepiped of points which are not part of the hand (namely, points located at a "compatible" depth, e.g. if the user 101 moves his hand very close to her/his bust), or portions of the wrist not required to capture the hand movements and which instead may be misleading in analyzing some types of movements (e.g. when the hand is repeatedly overstretched and closed, the centroid of the hand moves and consequently moves also the segmentation solid). Such points possibly unduly included in the segmentation solid will be excluded subsequently, as it will be discussed hereinafter.

From now on, the processing unit 105 will consider pixels excluded from the solid as certainly not part of the hand and pixels included in the solid as part of the hand. In particular, at a subsequent sub-step 504, the processing unit generates a validity mask, namely a N×M matrix of pixels wherein each pixel may assume two values: one value (e.g. 255) indicating that the pixel is part of the hand and the other value (e.g. 0) indicating that the pixel is not part of the hand.

At a subsequent sub-step 505, the processing unit 105 uses the validity mask for isolating a portion of the color frame, that will be named hereinafter as "validity area" or "segmented area", comprising only valid pixels (namely, those pixels that are considered as part of the hand). Similarly, the processing unit 105 preferably uses the validity mask for isolating a portion of the depth frame, that will be named hereinafter as "validity area" or "segmented area", comprising only valid pixels (namely, those pixels that are considered as part of the hand). The hand is accordingly segmented (namely, isolated from the rest of the scene) both in the color frame and in the depth frame. To this purpose, the processing unit 105 preferably considers each pixel of the color frame and, if the value corresponding to that pixel in the validity mask indicates that it is part of the hand, it preferably includes that pixel in the validity area of the color frame. Similarly, the processing unit 105 preferably considers each pixel of the depth frame and, if the value corresponding to that pixel in the validity mask indicates that it is part of the hand, it preferably includes that pixel in the validity area of the depth frame.

By referring again to the flow chart of FIG. 4, after the segmentation step 404 is completed, a color calibration step 405 is preferably carried out. As mentioned above, the color calibration step 405—together with the above described brightness calibration step 403—allows adjusting the operation of the system 100 to the actual lightning conditions of the environment, thereby allowing the system 100 to properly recognize the markers of the wearable device 102 based on their colors, independently of the lighting conditions. The color calibration step 405 will be now described in detail with reference to the flow chart of FIG. 6.

During a first sub-step 601, the processing unit 105 identifies a color calibration area in the color frame acquired by the video camera 103. The color calibration area is preferably a portion of the marker 202, more preferably the color calibration area is centered in the center of the marker 202. According to a preferred embodiment, such area is a squared area of 10×10 pixels in the color frame, centered in the center of the marker 202.

During a subsequent sub-step 602, the processing unit 105 determines the average color components of the color calibration area. In particular, each average color component (e.g. the average red component, in case of RGB components) is calculated as the average of that color component of all the pixels comprised within the color calibration area.

Then, during a subsequent sub-step 603, the processing unit 105 preferably determines an average brightness of the color calibration area. In particular, in case the color components are RGB components, the average brightness of the color calibration area is preferably calculated as the average of the three average RGB components calculated at sub-step 602.

Figure 6:
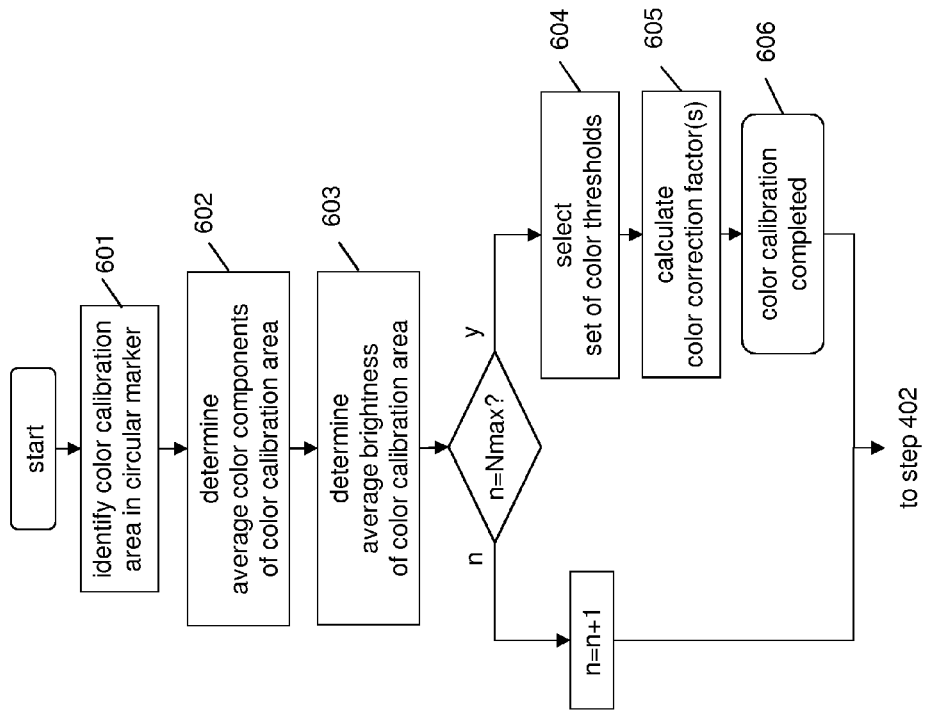
FIGS. 5, 6 and 7 are flow charts showing in further detail three steps of the flow chart of FIG. 4.

Sub-steps 601-602-603 are preferably iterated on a number Nmax of consecutive color frames. Accordingly, after sub-step 603 a check is made as to the number n of iterations reached. If the number is lower than the set number Nmax, the iteration number n is increased by one and the process goes back to the step 402 of acquisition of a new color frame and depth frame (FIG. 6 and FIG. 4). In particular, the inventors have found that sub-steps 601-602-603 shall be repeated on a number of consecutive color frames higher than 10, and more preferably higher than 30, for achieving a proper color calibration. This provides a more robust color calibration, which is immune from possible instabilities (namely, fluctuations and/or "spot" events) of the illumination conditions, thereby making the subsequent steps (which are based on color recognition techniques) very reliable and accurate. In particular, positive results were obtained by iterating sub-steps 601-602-603 on Nmax=50 consecutive color frames. Assuming that the frame rate of the video camera 103 is 30 fps, it follows that a proper color calibration is advantageously achieved within a very short period (a few seconds).

According to a preferred embodiment (not shown in FIG. 6), the processing unit 105 is configured to check whether sub-steps 601-602-603 are correctly carried out on a minimum number of color frames (e.g. 10) amongst the Nmax acquired color frames. Otherwise, if the processing unit 105 was not able to correctly carry out sub-steps 601-602-603 on the minimum number of color frames amongst the Nmax acquired color frames (e.g. because it was not able to recognize the marker 202), then the color calibration step 405 is started again, namely sub-steps 601-602-603 are preferably repeated on a subsequent block of Nmax consecutively acquired color frames.

After Nmax iterations of sub-steps 601-602-603 have been completed, during a subsequent sub-step 604, the processing unit 105 selects a set of color thresholds, that will be used for the recognition of the colors of the markers. To this purpose, the processing unit 105 preferably calculates an average of the values of average brightness of the color calibration area provided by the Nmax iterations of sub-step 603. This allows determining the amount of light that lightens the wearable device 102 (and, accordingly, the white marker 202). In particular, according to preferred embodiments, a number of (e.g. three) brightness ranges are preferably predefined: a lower range, a higher range and an intermediate range comprised between the lower range and the higher range. At sub-step 604, the processing unit 105 compares the average of the values of the average brightness of the color calibration area provided by the Nmax iterations of sub-step 603 (also termed "overall average brightness") with the predefined ranges. If the overall average brightness is comprised in the lower range, the processing unit 105 determines that the wearable device 102 is lightened by a "low light". If the overall average brightness is comprised in the higher range, the processing unit 105 determines that the wearable device 102 is lightened by a "high light". If the overall average brightness is comprised in the intermediate range, the processing unit 105 determines that the wearable device 102 is lightened by a "normal light". Then, the processing unit 105 selects a set of color thresholds on the base of the determined amount of light (low, normal, high). To this purpose, three different sets of color thresholds are preferably predefined and stored, e.g. in a XML file accessible by the processing unit 105. Each predefined set of color thresholds is associated to a respective amount of light (low, normal, high). Besides, each set of color thresholds comprises a number of sub-sets of color thresholds, one sub-set for each color of the markers of the wearable device 102, plus one sub-set for the background color of the wearable device 102. For instance, by referring to the glove 102 of FIGS. 2a and 2b, which comprises markers of 6 different colors, each one of the three sets of color thresholds comprises seven sub-sets of color thresholds, one for each marker color and one for the background color of the wearable device 102. A sub-set of color thresholds for a certain marker color (or wearable device background color) preferably comprises a lower color threshold and an upper color threshold for each color component. If the values of the color components of a certain pixel as detected by the video camera 103 are comprised between the respective lower and upper color thresholds of a certain sub-set for a certain marker color (or wearable device background color), the processing unit 105 determines that the pixel color is that marker color (or wearable device background color). The lower color threshold and upper color thresholds are preferably referred to the HSV (Hue, Saturation Value) color space. This is because the RGB color frames provided by the video camera 103 are preferably converted into the HSV color space before detection of the marker positions, as it will be discussed in detail herein after. Hence, at sub-step 604, the processing unit 105 selects, amongst the three sets of color thresholds, the one corresponding to the determined amount of light. This allows to choose the set of color thresholds which is most suitable for the actual illumination conditions of the environment in which the system 100 is operating.

Then, during a subsequent sub-step 605, the processing unit 105 preferably calculates one or more color correction factors to be applied to the color frames acquired by the video camera 103 before recognition of the markers of the wearable device 102 based on their colors. In particular, as described above, the Nmax iterations of sub-step 602 provide the average RGB components of the color calibration area of at most Nmax color frames. At sub-step 605, the processing unit 105 preferably calculates their averages, thereby providing a single overall average value for each color component. This calculation of the overall average color components of the color calibration area advantageously allows determining whether the light that lightens the environment (and that accordingly lightens also the white marker 202) has a dominant color component. Indeed, if the overall average color components of the color calibration area (which is nominally white in the exemplary embodiment) are balanced (namely, they have substantially the same value), this means that the light that lightens the environment has balanced color components too. If, however, the color calibration area has e.g. an overall average green dominant component (namely, the overall average green component has a value higher than the overall average red and blue components), this means that the light that lightens the environment has a green dominant component too. If the color of the calibration marker has been selected as being different from white, color calibration is preferably performed by comparing the detected color of the color calibration area with the expected color hue of the calibration marker 202, and identifying any unbalanced color components in the environment light. This shall be taken into account when the color of the markers is identified, as it will be described in detail herein after. Hence, if it is determined that the illumination conditions "shift" the theoretically white (or other) color of the color calibration area towards one of the color components (e.g. green) that is therefore dominant by a certain amount, the processing unit 105 determines a color correction factor to be applied to the color components of all the pixels of the color frames acquired by the video camera 103. The color correction factor for each color component in particular is a scaling factor by which the color component shall be multiplied in order to bring its value from the detected average value to its theoretical "balanced" value. This allows compensating possible imbalance of the color components due to the illumination conditions.

Color calibration is completed (step 606) upon completion of sub-steps 604 and 605.

Therefore, advantageously, the color calibration step 405—together with the above described brightness calibration step 403—allows adjusting the operation of the system 100 to the actual lightning conditions of the environment, thereby allowing the system 100 to properly recognize the markers of the wearable device 102 based on their colors, independently of the lighting conditions.

According to preferred embodiments, if color calibration cannot be completed by the processing unit 105 within a maximum number of consecutive iterations of steps 402-404-405 (for instance because the user 101 fails to hold the hand in the required position, so as the position of the marker 202 cannot be correctly determined), then the processing unit 105 preferably makes a predefined number of attempts to repeat the color calibration.

When the color calibration is completed, starting from the color frame acquired at the subsequent iteration of step 402, the processing unit 105 applies the color correction factor(s) determined at step 405 to the color frame (step 406). According to particularly preferred embodiments of the present invention, the color correction factor(s) are preferably applied only to the pixels of the validity area of the color frame, provided at sub-step 505. This advantageously reduces the calculation complexity of such step. Further, the color correction factor(s) calculated during the color calibration are preferably applied to the validity areas of all the subsequently acquired color frames, without repeating the color calibration during the whole motion capture session. It is indeed assumed that the illumination conditions do not change over the whole duration of the motion capturing session. If the illumination conditions suddenly change while the motion capturing session is ongoing, the user 101 shall stop the session and repeat the color calibration.

Then, according to particularly preferred embodiments, the processing unit 105 makes a conversion of the color components of the pixels of the color frame as provided by the video camera 103 and corrected at step 406 into the HSV (Hue Saturation Value) space (step 407). This color space is preferred to others (in particular, to the RGB space) because it is more robust to brightness variations. Preferably, this step can be performed only on the pixels of the validity area of the color frame.

Figure 7:
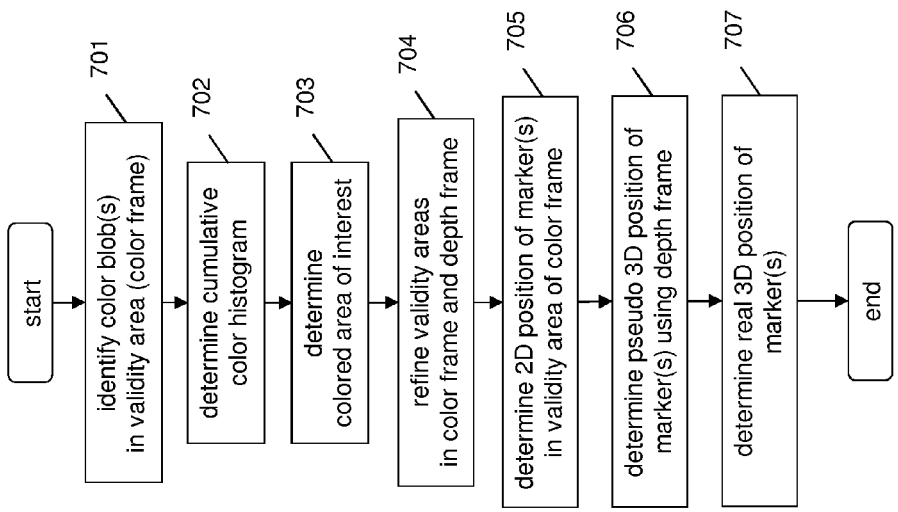

Then, the processing unit 105 preferably detects the position in the three-dimensional space of the markers of the wearable device 102 based on their colors (step 408). This step will be described in further detail hereinafter, with reference to the flow chart of FIG. 7.

During a first sub-step 701, the processing unit 105 preferably identifies, within the validity area of the color frame isolated at sub-step 505, at least one "color blob", namely a group of contiguous pixels having a certain marker color or wearable device background color. To this purpose, for each pixel of the color frame comprised within the validity area, the processing unit 105 preferably compares the corresponding color components (that, as mentioned above, are HSV coordinates) with the color thresholds selected at sub-step 604. In particular, as described above, the set of color thresholds selected at sub-step 604 comprises a number of sub-sets of color thresholds, one for each marker color and one for the wearable device background color. Assuming that the wearable device 102 comprises six markers of six different colors, the set of color thresholds comprises seven sub-sets of color thresholds, one for each marker color and one for the wearable device background color. A sub-set of color thresholds for a certain marker color or wearable device background color preferably comprises a lower color threshold and an upper color threshold for each color component. Hence, for determining whether a pixel of the validity area belongs to a color blob having a certain marker color or wearable device background color, the processing unit 105 preferably checks whether each one of the color components of the considered pixel lies within the range defined by lower and upper color thresholds for that component. In the affirmative, the processing unit 105 concludes that the pixel is part of the color blob. Advantageously, since the determination of the color blobs is confined to the validity area of the color frame (namely, the pixels of the color frame that lie out of the validity area are not considered when color blobs are searched), there is no risk to identify as a color blob an item of the scene that accidentally has the same color as one of the markers or the background color of the wearable device 102. Hence, at the end of sub-step 701, the processing unit 105 has identified one color blob for each marker color, each color blob corresponding to a respective marker of the wearable device 102. Further, the processing unit 105 has identified a color blob for the background color of the wearable device, that corresponds to the "body" of the wearable device 102. It shall be further noticed that, since the color thresholds have been selected at sub-step 604 based on the amount of light that lightens the scene and the validity area of the color frame has been corrected at step 406 by the color correction factor(s) calculated at sub-step 605, the identification of the color blobs is properly executed independently of the properties (brightness and color) of the light that illuminates the wearable device 102.

Then, during a subsequent sub-step 702, the processing unit 105 preferably calculates a color histogram for each one of the color blobs identified at sub-step 701 and a cumulative color histogram of the wearable device 102 with markers. As known, the color histogram of a digital frame (or a portion thereof) represents the number of pixels of the frame (or frame portion) that have colors in each of a fixed list of color ranges. In particular, for each marker color and background color of the wearable device, the range of values that each color component may assume is divided into several (preferably, 16) sub-ranges (also termed "bins"), and then the number of pixels of the color blob whose color component lies within each bin is calculated. Hence, the color histogram of each color blob provides the color distribution of the pixels belonging to that color blob. The cumulative color histogram of the wearable device 102 with markers is then obtained by merging the color histograms determined for the color blobs. The cumulative color histogram accordingly exhibits peaks at the marker colors and background color.

Then, during a subsequent sub-step 703, the processing unit 105 preferably uses the cumulative color histogram obtained at sub-step 703 to determine a "colored area of interest" within the validity area of the color frame. Preferably, the colored area of interest is formed by those pixels that, amongst all the pixels of the validity area of the color frame, have a higher probability of belonging to the cumulative color histogram. In particular, for each pixel of the validity area of the color frame, a probability value is calculated of belonging to the cumulative color histogram. The probability values are preferably discretized (e.g. 256 discrete probability values may be defined, from 0 to 255). Since the pixels representing the wearable device 102 with its markers are those with the higher probability of belonging to the cumulative color histogram (whereas the other pixels of the validity area have a much lower probability of belonging to the color histogram), the two-dimensional probability mapping of the validity area defines a colored area of interest which basically is a two-dimensional projection of the wearable device 102. According to preferred embodiments, sub-step 703 is carried out using the known CAMshift algorithm described e.g. in "Learning OpenCV", G. Bradski, A. Kaelher, O'Reilly, pages 337-341. Since the CAMshift algorithm is applied only to the validity area of the color frame, advantageously there is not risk to include in the colored area of interest pixels not representing the wearable device 102 and accidentally having the same color as the wearable device 102 or one of its markers.

Then, during a subsequent sub-step 704, the processing unit 105 preferably determines the contour of the wearable device 102 as the perimeter of the colored area of interest, and preferably uses the contour for "refining" the validity areas in the color frame and depth frame as determined at the segmentation step 404 (see sub-step 505). Indeed, the validity areas in the color frame and depth frame have been determined at sub-step 505 basically using depth information only, and may accordingly include (especially at the edges of the projection of the wearable device 102) pixels which are not part of the wearable device 102 but have substantially the same distance from the range camera 104 as the wearable device 102, e.g. the wrist portion not covered by the wearable device 102 and/or part of the bust of the user 101 (when the user 101 moves the hand very close to her/his bust). Sub-step 704 allows excluding such pixels from the validity areas of both the color frame and the depth frame, thereby making the detection of the position of each marker very robust and reliable, by verifying that the position of each marker lies within the "refined" validity area.

Then, during a subsequent sub-step 705, the processing unit 105 preferably determines the two-dimensional position of each marker of the wearable device 102. Preferably, the two-dimensional position of a marker having a certain marker color is determined by considering the corresponding color blob identified at sub-step 701, determining the smallest square capable of containing the whole color blob and determining the center of the square. The two-dimensional position of the marker is then preferably provided in the form of row number and column number ($x_{pixel}$, $y_{pixel}$) of the center of the square within the N×M color frame.

Then, during a subsequent sub-step 706, the processing unit 105 preferably determines a pseudo three-dimensional position for each marker of the wearable device 102. In particular, since as mentioned above, each color frame and corresponding depth frame have the same size N×M, the pseudo three-dimensional position for each marker is provided by the row number and column number ($x_{pixel}$, $y_{pixel}$) determined at sub-step 705 and, in the third dimension, by the depth $z_{mm}$ ($x_{pixel}$, $y_{pixel}$) retrieved from the depth frame at the same row number and column number ($x_{pixel}$, $y_{pixel}$).

Then, during a subsequent sub-step 707, the processing unit 105 preferably converts the pseudo three-dimensional position of each marker into a real three-dimensional position, namely a tern of real coordinates that indicate the position of the marker in the real three-dimensional space. The real coordinates are referred to a Cartesian coordinate system, depending on the type of range camera 104 used. In particular, the conversion comprises a projection that takes into account the distance from the range camera 104, the projection center and the focal lengths of the objective comprised in the range camera 104. Even more particularly, the following conversion equations are for example applied:

$$x_{mm} = \left(\frac{x_{pixel}}{W} - 0.5\right) * z_{mm}(x_{pixel}, y_{pixel}) * \tan\left(\frac{HFOV}{2}\right) * 2 \quad [1]$$

$$y_{mm} = \left(0.5 - \frac{y_{pixel}}{H}\right) * z_{mm}(x_{pixel}, y_{pixel}) * \tan\left(\frac{VFOV}{2}\right) * 2 \quad [2]$$

where (W, H) are the spatial resolutions of the range camera 104 along the directions x and y, whereas (HFOV, VFOV) are the field of view angles (horizontal and vertical) of the range camera 104, that depend on the spatial resolutions (W, H) and the focal length $f_L$ of the range camera 104 according to the following equations:

$$HFOV = 2 * \arctan\left(\frac{0.5 * W}{f_L}\right) \quad [3]$$

$$VFOV = 2 * \arctan\left(\frac{0.5 * H}{f_L}\right) \quad [4]$$

By referring again to FIG. 4, after the three-dimensional position of each marker has been determined, at step 409 the processing unit 105 preferably stores it in a memory device. The memory device may be either a local device (namely, it may be integral with other components of the system 100, e.g. the processing unit 105). Alternatively, the memory device may be a remote device to which the processing unit 105 is connected, e.g. via the Internet. The marker positions may be logged in a file.

Hence, by iterating steps 404, 406, 407, 408 and 409 for each color frame and depth frame acquired while the user 101 is moving, the processing unit 105 is advantageously capable of determining (and storing) the three-dimensional positions in the real space of all the markers of the wearable device 102. The ordered sequence of the three-dimensional positions assumed by a marker basically amounts to the three-dimensional trajectory of that marker. The ordered sequence of positions of a marker may be logged in a textual form or a graphical form in the above mentioned file. Alternatively or in addition, the ordered sequence of positions may be used for generating a video showing the three-dimensional trajectory of the marker.

The condition upon which iteration of steps 402, 404, 406, 407, 408 and 409 is stopped depends on the operating mode of the system 100. The iteration may be automatically stopped, e.g. after a predefined time has elapsed since the beginning of the motion capture session. Alternatively, the user 101 may manually input (e.g. via the graphic user interface displayed by the display 106) a command to stop the execution.

The system 100 therefore basically captures the movements of the body portion covered by the wearable device 102 with markers, by making a combined use of color information and depth information. In particular, as described above, before the color calibration is carried out, the system 100 firstly uses exclusively depth information for isolating a rough validity area that contains the projection of the wearable device 102 from the rest of the scene (see segmentation step 404). Then, after the color calibration is completed, the system 100 uses color information for refining the shape of the validity area (see sub-steps 702, 703, 704 of step 408) and for identifying the two-dimensional marker positions (see sub-steps 701, 705 of step 408), the search of the markers being confined to the isolated validity area. Finally, the system 100 uses again depth information for determining the three-dimensional marker positions (see sub-step 706 of step 408).

By alternating depth-based analysis and color-based analysis, the algorithm executed by the system 100 is therefore advantageously capable of gradually refining the three-dimensional positions of the wearable device 102 and its markers, thereby capturing in real-time the movements of the body part covered by the wearable device 102 in a very robust and accurate way. The inventors have estimated that the accuracy of the system 100 is high enough to enable the calculation of kinematic parameters, which may be used e.g. for diagnosing neurodegenerative diseases and/or tracking their progression, as it will be described in detail hereinafter.

The robustness and accuracy of the system 100 is also due to the brightness calibration and color calibration, which are automatically performed by the system 100 before starting the motion capturing. These operations enable the system 100 to identify the markers based on their colors in a reliable and accurate way, independently of the illumination conditions of the surrounding environment.

The robustness and accuracy of the system 100 is also due to the use of the wearable device 102 with markers. First of all, the wearable device 102 has a uniform color (except the markers) that, especially when it is black, is independent of the illumination conditions. This eases the color-based identification of the contour of the wearable device 102, see sub-step 703. Further, the position, color, shapes of the markers may be chosen in a very flexible way, based on the type of movements that shall be captured. Further, markers may be easily added or removed, thereby making the wearable device 102 "scalable" as needed. Further, the wearable device 102 does not hamper the movements of the user 101 and makes the system 100 as a whole substantially non-invasive. The wearable device 102, on the other hand, may be easily worn by the user 101 in an autonomous way.

Actually, the system 100 as a whole can be easily used by the user 101, without the need of any assistance by a specialized operator. Calibrations of the system 100 are indeed very short steps, which require a minimum support from the user 101. In particular, brightness calibration is completely automatic and transparent to the user 101. As to color calibration, it simply requires that the user holds his/her body part covered by the wearable device 102 roughly in a certain position for a very short period (a few seconds). This is a very simple operation, that may be carried out also by a user 101 whose suffers from motor difficulties such as tremors.

Moreover, the system 100 has advantageously a reduced cost, since all its components (the wearable device, the processing unit, the video camera and the range camera) have a very reduced cost.

Hereinafter, the operation of the processing unit 105 when it executes the second block 302 of the software program will be described in detail.

As mentioned above, the second block 302 is preferably configured to receive the three-dimensional trajectories of the markers and process them for calculating one or more kinematic quantities (e.g. change of position, speed, acceleration, rate, frequency, etc.) relating to the movement of the body portion covered by the wearable device 102.

More particularly, the second block 302 is preferably configured to calculate at least one kinematic quantity (e.g. amplitude, range, speed, duration, rate, frequency, etc.) which are considered relevant for analyzing the movement, over the whole duration of it. For instance, when the movement (or exercise) that the user 101 shall carry out consists in iterating several time a predefined movement, each single iteration of the movement is preferably isolated and individually analyzed for calculating the relative kinematic quantities. The kinematic quantities may be calculated by taking into account the three-dimensional trajectory of a single marker or the combination of the three-dimensional trajectories of multiple markers of the wearable device 102. The ensemble of the kinematic quantities calculated for each iteration of the movement therefore describes the movement as a whole and for its whole duration.

The second block 302 is preferably configured to process each one of such kinematic quantities for providing either a value measurement (e.g. calculate an average, maximum or minimum value of the kinematic quantity) and/or a regularity measurement (e.g. calculating a variation coefficient or standard deviation of the kinematic quantity). Both the value measurement and the regularity measurement may be carried out over the whole duration of the movement. Alternatively or in addition, the duration of the movement is divided in at least two timeslots, and a value measurement and/or a regularity measurement is provided for each timeslot separately.

Preferably, the second block 302 is also configured to process the kinematic quantities in order to calculate their trend, namely their variations over time. To this purpose, the second block 302 preferably uses a linear or quadratic regression technique. Also this trend analysis may be carried out on the whole duration of the movements and/or in multiple timeslots of the movement duration.

FIGS. 8a, 8b, 8c and 8d are some exemplary graphs showing the results of the calculations carried out by the second block 302.

Figure 8A:
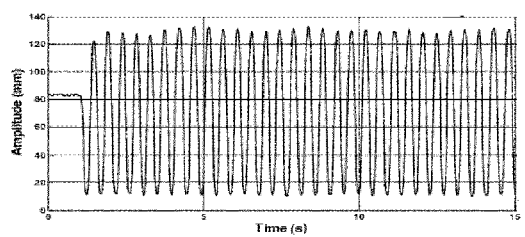
FIGS. 8a to 8d are graphs showing results obtained with the system of the present invention.

FIG. 8a is a graph of the amplitude obtained by capturing a "finger tapping" movement (namely, forefinger and thumb are repeatedly brought into reciprocal contact and then pulled away). The amplitude graph shown in FIG. 8a was obtained from the combination of the three-dimensional trajectories of the markers 203 and 204 shown in FIGS. 2a and 2b. The alternating approaching and moving away of the fingers over time is clearly visible in FIG. 8a. The velocity of the movement, which is shown in FIG. 8b, was calculated as the first derivative of the amplitude curve of FIG. 8a.

Figure 8C:
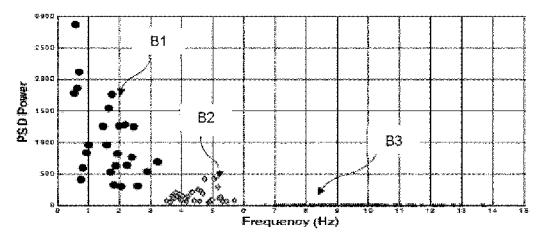
Figure 8B:
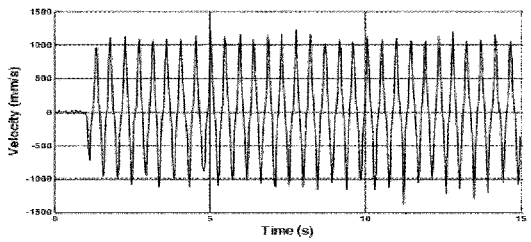

FIG. 8c is a graph showing the results of a frequency analysis of the same movement, carried out on three different frequency bandwidths B1, B2, B3 that correspond to three different "components" of the movement (namely, voluntary motion component, tremor and physiological movement). The presence of peaks in the first bandwidth B1 indicates a high number of rate variations during execution of the finger tapping movement. The presence of peaks in the second bandwidth B2 indicates the presence of tremors (also when no finger tapping movement is executed). The third bandwidth B3 corresponding to the physiological movement usually does not comprise any peak.

Figure 8D:
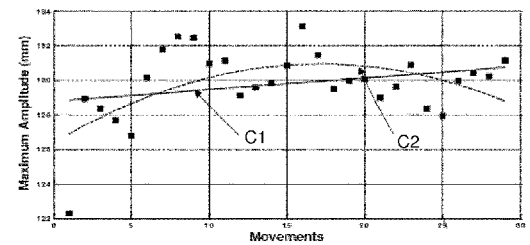

FIG. 8d is a graph showing the results of an exemplary trend analysis of the maximum amplitude values shown in FIG. 8a. The maximum amplitudes of all the iterations of the finger tapping movement (which are shown in the graph of FIG. 8d) have been used for both a linear regression and a quadratic regression analysis. The trend curves are calculated over the whole duration of the movement. The obtained trend curves C1 and C2 are depicted in FIG. 8d and provide an indication of the movement trend during the whole observation period. In particular, the quadratic trend curve C2 shows that the performance (in terms of amplitude of the movement) during a central slot of the observation period was better than in the initial and final slots. Based on such first quantitative trend analysis over the whole observation period, the observation period may be divided in timeslots (e.g. three timeslots, each timeslot having a duration of about ⅓ of the whole observation period, the second timeslot being the "best performance" one) and further statistical analysis may be carried out on each timeslot separately for evaluating the performance in a more detailed way.

Hereinafter, the operation of the processing unit 105 when it executes the third block 303 of the software program will be described in detail.

As mentioned above, the third block 303 is preferably configured to receive the one or more kinematic quantities calculated by the second block 302 and to process them for extrapolating quantitative information on the motor skills of the user 101 and, possibly, the presence and seriousness of a neurodegenerative disease (e.g. Parkinson's disease).

In particular, the third block 303 is preferably configured to analyse the kinematic parameters for studying some specific motor difficulties of the user 101, e.g. due to a specific neurodegenerative disease (e.g. Parkinson's disease), ageing, injuries, etc. By referring for instance to the Parkinson's disease, the above mentioned UPDRS defines a specific set of motor exercises. Evaluating the motor skills of the user 101 in executing these exercises in terms of general features of the movements (amplitude, velocity, rate, etc.), value measurements and/or regularity measurements, trend analysis and detection of anomalous events (e.g. freezing, interruptions or wavering, missing closure of forefinger and thumb during finger tapping, etc.) provides a quantitative indication of the seriousness of the disease.

Figure 9A:
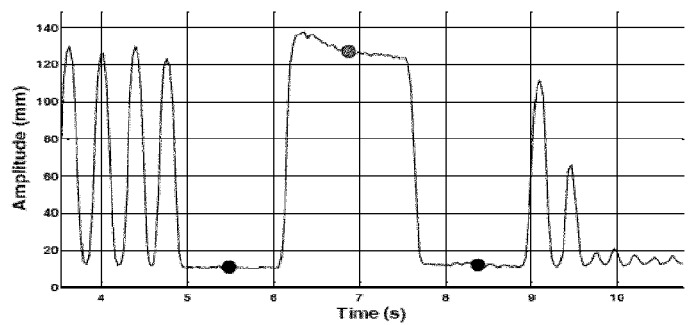
FIGS. 9a and 9b are graphs showing results obtained with the system of the present invention.

The third block 303 is therefore preferably configured to detect the above anomalous events by suitably analysing the three-dimensional trajectories of one or more markers (see FIG. 9a showing an amplitude graph where three consecutive "freezings" are clearly visible).

Figure 9B:
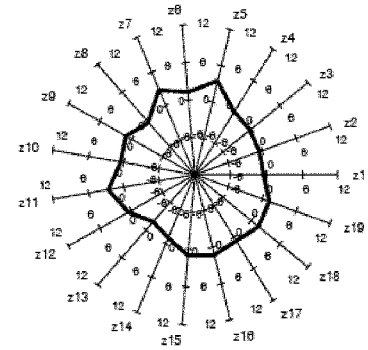

Further, the third block 303 is also configured to extract at least one most significant kinematic quantity amongst those calculated by the second block 302 (preferably using a PCA, Principal Component Analysis. The at least one most significant kinematic quantity is then preferably represented in a radar graph, which is particularly compact and intuitive and provides an indication of the motor difficulties. An exemplary radar graph is depicted in FIG. 9b. In FIG. 9a, the references $z1, z2 \ldots z19$ indicate the most significant kinematic quantities for the evaluation of the progression of a certain disease. The measured value of each most significant kinematic quantity is represented on the respective axis by a point. The radar graph is obtained by joining all the points with a continuous line. The value of each most significant kinematic quantity is preferably normalized (namely, divided by) a reference value, which was obtained from reference sample(s) (e.g. one or more healthy user). Hence, when the radar line intersects the axis of a certain most significant kinematic quantity on a circumference having unitary radius, it indicates that the value of that quantity is equal to the reference value. The more the value of a certain most significant kinematic quantity differs from the respective reference value, the farther the intersection between radar line and axis of that kinematic quantity is from the unitary circumference. Hence, when the radar line is closer to the unitary circumference, the motor difficulties of the user 101 are less serious. The radar graph also provides an immediate and intuitive indication of the most significant kinematic quantity(ies) which mostly depart from their reference values (e.g. amplitude, frequency, etc.) during the motor exercise, that correspond to the points where the radar line departs more from the unitary circumference. Other types of graphs may however be used for representing the values of the most significant kinematic quantities, e.g. a linear graph. On a linear graph, the most significant kinematic quantity(ies) which mostly depart from their reference values would be represented by peaks or troughs.

Hence, by using kinematic quantities derived from a reference sample for training a "classifier" (e.g. a Bayesian classifier) capable of associating a set of quantities to a well-defined medical evaluation of the seriousness of the disease (typically represented by a discrete set of classes), the classifier may analyse the set of most significant kinematic quantities referring to the user 101 by performing an evaluation prediction, indicating a probability to belong to a certain class. The most significant kinematic quantities are preferably locally or remotely stored by the system 100, as well as their graphic representation. This allows monitoring the progression of the disease, comparing the motor difficulties and seriousness of the disease in users subjected to a same pharmacological treatment, etc.

According to other variants, the system 100 may also be configured to:
  check whether the movement of the body portion covered by the wearable device 102 is correct. For instance, if the user 101 is requested to execute a predefined exercise (e.g. the finger tapping exercise), the system 100 may be configured, upon completion of the exercise, to check whether it was correctly executed by the user 101 by analysing the three-dimensional trajectories of one or more markers of the wearable device 102 and check if they correspond to the expected ones;
  display the movements executed by the user 101 wearing the wearable device 102 on the display 106, e.g. in a window that displays in real time the calculated three-dimensional trajectories of the markers, e.g. by means of colored lines;
  provide the user 101 with a qualitative or quantitative indication of his performance in the execution of the exercise. In this respect, the system 100 may operate either in a time-based mode (namely, by setting a maximum time upon which the exercise shall be completed) or in an event-based mode (namely, by setting a certain number of iterations of the movements to be executed). By analysing the marker three-dimensional trajectories upon completion of the exercise, the system 100 may determine whether the exercise was completed within the maximum time and/or if the requested number of iterations have been executed, and provide a feedback to the user 101 in this connection. By analysing some kinematic parameters, the system 100 is also preferably capable to compare the performance of the user 101 (namely, determining whether the movements were executed too slowly, with an insufficient amplitude or rate, etc.) and provide a quantitative evaluation of the performance of the user 101, e.g. on a scale ranging from 1 to 10 determined on the basis of the performance of a number of reference sample users;

support a motor rehabilitation session, namely the execution of one or more predefined motor exercises specifically aimed at improving the motor skills of the user 101. The system 100 may be set in this operation mode e.g. during the initialization step 401. When the system 100 is brought in such operation mode, the system 100 preferably presents the user 101 (e.g. via the display 106) at least one exercise to be executed. When the system 100 is brought in such mode, the operation of the first and second blocks 301 and 302 is substantially the same as described above. The third block 303 instead is replaced by a block that evaluates the motor skills of the user 101 from a rehabilitation point of view.

In summary, the motion capture system according to the present invention, by making a combined use of a wearable device with colored markers and a processing unit configured to perform a brightness and color calibration and to determine the three-dimensional trajectories of the markers using both color information and depth information, is very robust and accurate, and is accordingly particularly suitable for applications in the medical field, where it constitutes a low cost, non invasive and reliable tool providing an objective and accurate evaluation of the motor skills of patients.

The invention claimed is:

1. A motion capture system comprising:
   a wearable device configured to be fitted on at least a part of a body of a user, said wearable device comprising at least one marker having a predetermined marker color;
   a video camera configured to acquire at least one color frame of a scene comprising said wearable device, said at least one marker being visible in said at least one color frame;
   a range camera configured to acquire at least one depth frame of said scene; and
   a processing unit configured to receive said at least one color frame from said video camera and said at least one depth frame from said range camera, to process said at least one depth frame for identifying in said at least one color frame a validity area comprising pixels representing said wearable device, to search said at least one marker in said at least one color frame based on said marker color, said search being confined to said validity area, and to capture a motion of said part of the body of said user based on a sequence of positions of said at least one marker.

2. The system according to claim 1, wherein said wearable device is made of a flexible and opaque material.

3. The system according to claim 1, wherein said wearable device has an external surface having a background color different from said marker color.

4. The system according to claim 1, wherein said wearable device comprises at least two markers, said at least two markers comprising a color calibration marker whose marker color is white.

5. The system according to claim 1, wherein said processing unit is configured to perform a brightness calibration, before searching said at least one marker in said at least one color frame, said brightness calibration comprising adjusting a gain of said video camera so as to bring an average brightness of said at least one color frame within a predefined range.

6. The system according to claim 4, wherein said processing unit is configured to identify said validity area in said at least one color frame by:
   identifying said color calibration marker in said at least one color frame, based on its shape;
   determining a two-dimensional position of a center of said color calibration marker in said at least one color frame and a depth of said center of said color calibration marker in said at least one depth frame;
   identifying in said at least one depth frame a cluster of pixels whose depth is substantially the same as said depth of said center of said color calibration marker and determining a centroid of said cluster;
   constructing a segmentation solid around said centroid of said cluster, said segmentation solid having shape and size suitable for containing said wearable device when fitted on said at least a part of said body of said user, independently of a current position of said at least a part of said body of said user; and
   identifying said validity area in said at least one color frame as a portion of said color frame formed by pixels included in said segmentation solid.

7. The system according to claim 1, wherein said processing unit is configured to perform a color calibration, before searching said at least one marker in said at least one color frame, said color calibration comprising one or more of calculating one or more color correction factors to be applied to said at least one color frame and selecting a set of color thresholds to be used for searching said at least one marker in said validity area of said at least one color frame.

8. The system according to claim 7, wherein said processing unit is configured to calculate said one or more color correction factors by:
   identifying a color calibration marker in said at least one color frame, based on its shape;
   calculating average color components of a portion of said color calibration marker; and
   calculating said one or more color correction factors to be applied to said at least one color frame based on said average color components of said portion of said color calibration marker.

9. The system according to claim 7, wherein said processing unit is configured to select said set of color thresholds to be used for searching said at least one marker in said validity area of said at least one color frame by:
   identifying said calibration marker in said color frame, based on its shape;
   calculating an average brightness of a portion of said color calibration marker; and
   selecting said set of color thresholds based on said average brightness of said portion of said color calibration marker.

10. The system according to claim 7, wherein said processing unit is configured to apply said one or more color correction factors only to said validity area of said at least one color frame, before searching said at least one marker in said validity area of said at least one color frame based on said marker color.

11. The system according to claim 1, wherein said processing unit is configured to search said at least one marker in said validity area of said at least one color frame by identifying, within said validity area of said at least one color frame, at least one marker color blob formed by contiguous pixels having said marker color.

12. The system according to claim 11, wherein said processing unit is further configured to determine a three-dimensional position of said at least one marker by processing both said at least one color frame and said at least one depth frame.

13. The system according to claim 12, wherein said processing unit is configured to determine said three-dimensional position of said at least one marker by:
 determining a two-dimensional position of a center of said at least one marker color blob in said at least one color frame;
 determining a pseudo-three dimensional position of said at least one marker, said pseudo-three dimensional position comprising said two-dimensional position of said center of said at least one marker color blob in said at least one color frame and a depth of said center of said at least one marker color blob in said at least one depth frame; and
 converting said pseudo-three dimensional position of said at least one marker into a tern of coordinates that indicate said three-dimensional position of said at least one marker relative to a Cartesian coordinate system.

14. The system according to claim 3, wherein said processing unit is further configured to refine said validity area of said at least one color frame using color information.

15. The system according to claim 14, wherein said processing unit is configured to refine said validity area of said at least one color frame by:
 identifying, within said validity area of said at least one color frame, at least one marker color blob formed by contiguous pixels having said marker color;
 identifying, within said validity area of said at least one color frame, a background color blob formed by contiguous pixels having said background color;
 calculating a separate color histogram for each one of said at least one marker color blob and said background color blob;
 calculating a cumulative color histogram by merging said separate color histograms for said at least one marker color blob and said background color blob; and
 refining said validity area of said at least one color frame by excluding from said validity area those pixels whose probability of belonging to said cumulative color histogram is substantially null.

16. A method for capturing motion of at least part of a body of a user upon which a wearable device is fitted, said wearable device comprising at least one marker having a predetermined marker color, said method comprising:
 a) receiving, from a video camera, at least one color frame of a scene comprising said wearable device, said at least one marker being visible in said at least one color frame;
 b) receiving, from a range camera, at least one depth frame of said scene;
 c) processing said at least one depth frame for identifying in said at least one color frame a validity area comprising pixels representing said wearable device;
 d) searching said at least one marker in said at least one color frame based on said marker color, said search being confined to said validity area; and
 e) capturing a motion of said part of the body of said user based on a sequence of positions of said at least one marker.

17. A computer readable medium including software code portions stored thereon that, when executed by a computer, perform a method for capturing motion of at least part of a body of a user upon which a wearable device comprising at least one marker having a predetermined marker color is fitted, the method comprising the steps of:
 a) receiving, from a video camera, at least one color frame of a scene comprising said wearable device, said at least one marker being visible in said at least one color frame;
 b) receiving, from a range camera, at least one depth frame of said scene;
 c) processing said at least one depth frame for identifying in said at least one color frame a validity area comprising pixels representing said wearable device;
 d) searching said at least one marker in said at least one color frame based on said marker color, said search being confined to said validity area; and
 e) capturing a motion of said part of the body of said user based on a sequence of positions of said at least one marker.

\* \* \* \* \*